United States Patent [19]
Swain et al.

[11] Patent Number: 5,755,730
[45] Date of Patent: May 26, 1998

[54] DEVICE FOR USE IN CUTTING THREADS

[75] Inventors: Paul Swain; Feng Gong; Timothy N. Mills, all of London, United Kingdom

[73] Assignee: University College London, London, United Kingdom

[21] Appl. No.: 714,103

[22] PCT Filed: Mar. 23, 1995

[86] PCT No.: PCT/GB95/00653

§ 371 Date: Nov. 29, 1996

§ 102(e) Date: Nov. 29, 1996

[87] PCT Pub. No.: WO95/25470

PCT Pub. Date: Sep. 28, 1995

[30] Foreign Application Priority Data

Mar. 23, 1994 [GB] United Kingdom ............ 9405791

[51] Int. Cl.$^6$ .................................................. A61B 17/04
[52] U.S. Cl. .................... 606/148; 606/167; 606/170
[58] Field of Search ............................ 606/139, 148, 606/167, 169, 170

[56] References Cited

U.S. PATENT DOCUMENTS

| | | | |
|---|---|---|---|
| 2,521,161 | 9/1950 | Grover | 606/148 |
| 4,038,988 | 8/1977 | Perisse | 606/606 |
| 4,961,741 | 10/1990 | Hayhurst | 606/139 |
| 5,084,058 | 1/1992 | Li | 606/148 |
| 5,087,263 | 2/1992 | Li | 606/148 |
| 5,100,415 | 3/1992 | Hayhurst | 606/148 |
| 5,112,299 | 5/1992 | Fascaloff | 606/170 |
| 5,133,723 | 7/1992 | Li et al. | 606/148 |
| 5,163,946 | 11/1992 | Li | 606/148 |
| 5,176,691 | 1/1993 | Pierce | 606/148 |
| 5,192,287 | 3/1993 | Fournier et al. | |
| 5,217,471 | 6/1993 | Burkhart | |
| 5,234,444 | 8/1993 | Christoudias | |
| 5,269,791 | 12/1993 | Mayzels et al. | |
| 5,292,327 | 3/1994 | Dodd et al. | |
| 5,320,629 | 6/1994 | Noda et al. | |
| 5,324,298 | 6/1994 | Phillips et al. | |
| 5,334,200 | 8/1994 | Johnson | |
| 5,397,326 | 3/1995 | Mangum | |
| 5,403,330 | 4/1995 | Tuason | |
| 5,423,837 | 6/1995 | Meicle et al. | 606/148 |
| 5,439,470 | 8/1995 | Li | |
| 5,549,618 | 8/1996 | Fleenor | 606/167 |
| 5,562,684 | 10/1996 | Krammerer | |
| 5,571,117 | 11/1996 | Ahn | |
| 5,601,576 | 2/1997 | Garrison | |

FOREIGN PATENT DOCUMENTS

| | | |
|---|---|---|
| 0706779 | 4/1996 | European Pat. Off. |
| 2 247 841 | 9/1991 | United Kingdom |
| WO94/05220 | 3/1994 | WIPO |

Primary Examiner—Gary Jackson
Attorney, Agent, or Firm—Arthur Z. Bookstein; John F. Perullo

[57] ABSTRACT

A device is provided for cutting threads, particularly curing surgery carried out using an endoscope. The device has a cutting member having at least one aperture extending therethrough of a size sufficient to permit the surgical thread to slide therethrough, the aperture having a thread-cutting edge. In use, the cutting member is located at the distal end of an endoscope.

13 Claims, 2 Drawing Sheets

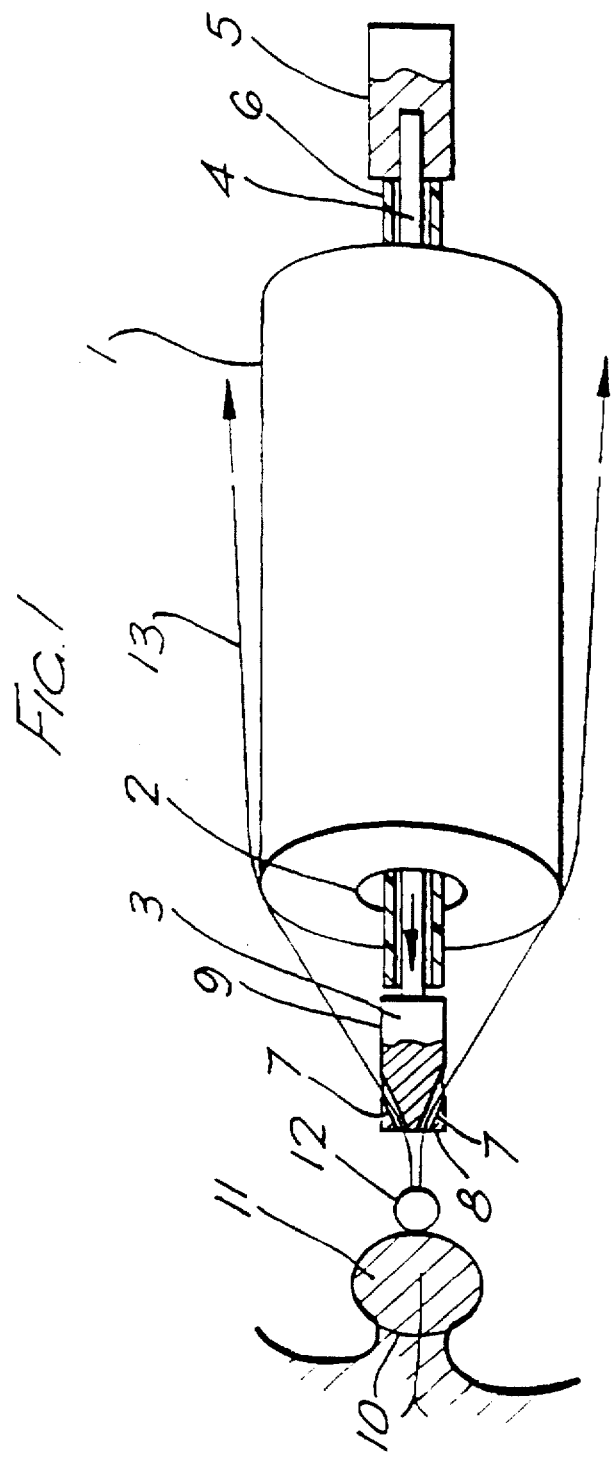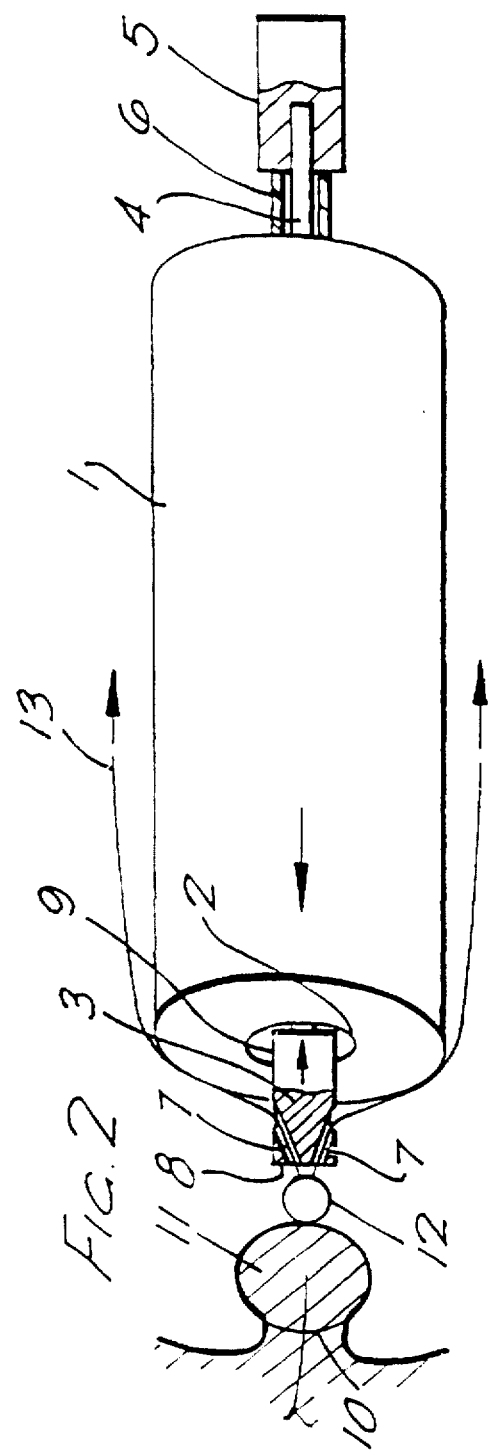

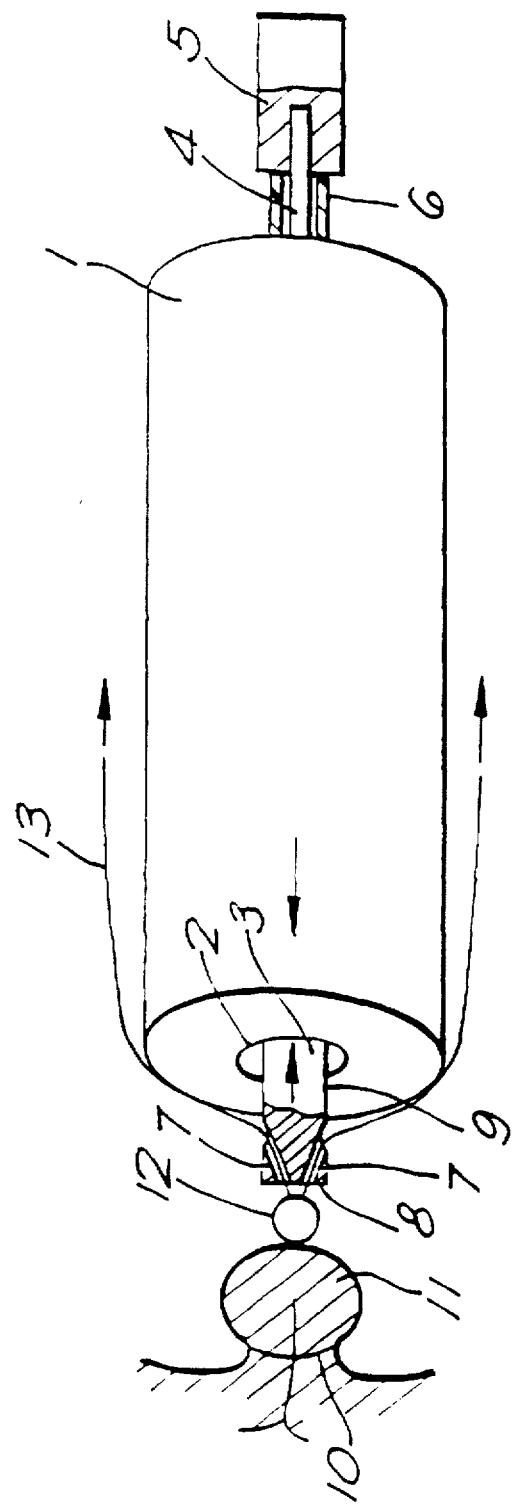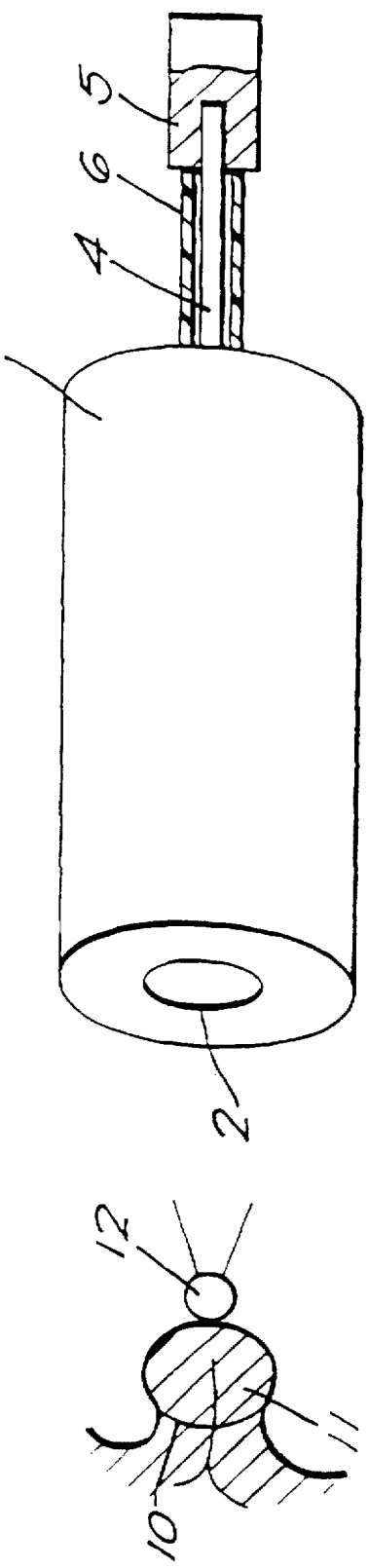

DEVICE FOR USE IN CUTTING THREADS

This invention relates to a device for use in cutting threads. It is particularly for use in cutting threads during surgery, and, more particularly, in surgery carried out using an endoscope. A primary intended field of application of the invention is in surgery carried out using a flexible endoscope, though it is applicable also to surgery where a rigid endoscope is used.

In conventional surgery, the threads used, for example, in forming sutures, are normally cut using scissors. However, this option may not be open to someone carrying out surgery down a flexible endoscope. In such surgery the surgical tools used are located at the distal end of the endoscope, and must normally be manipulated by control means extending down a channel in the endoscope. Manipulating conventional scissors in this way is at least difficult, and may be impossible. It is also known to use a guillotine, but no satisfactory guillotine is believed currently to exist for endoscopic use.

According to the present invention there is provided a device for use in cutting a surgical thread, which comprises a cutting member having at least one aperture extending therethrough of a size sufficient to permit the surgical thread to slide therethrough, the aperture having a thread-cutting edge, and means for enabling the cutting member to be located at the distal end of an endoscope.

An embodiment of the invention will now be described in more detail, with reference to FIGS. 1 to 4 of the accompanying drawings, which show successive stages in the use of the embodiment.

FIG. 1, like the other drawings, is diagrammatic, and shows the distal end portion of an endoscope 1 having a biopsy channel 2 through which a thread cutter according to the present invention can pass. In practice, of course, the endoscope would have other features, for example a viewing channel, but these are not shown and are assumed to be conventional.

The thread cutter according to the present invention comprises a cutting member 3 mounted on the distal end of a flexible wire 4. By way of example, the wire 4 can be a 1 mm wire made of steel of a surgically acceptable type. In an alternative embodiment, the wire 4 may be replaced by a Bowden cable. The proximal end of the wire is fixed in a mounting member 5, which is of a suitable size and shape to be grasped by the surgeon during use of the thread cutter. The wire 4 is surrounded by a plastics tube 6 which is not connected either to the cutting member 3 or the mounting member 5, and in which the wire 4 is freely slidable. The tube 6 is preferably made of polytetrafluoroethylene, or other material having a low coefficient of friction, and is intended to enable the cutting member and its wire to be readily passed down the channel 2, and withdrawn therefrom. It must be kept in mind that, in practice, the endoscope 1, when in position in a patient, will have a number of bends in it, and care therefore needs to be taken to ensure that the cutting member and its wire can move freely along the channel 2, despite the presence of these bends.

The cutting member 3 is provided with two apertures 7 which extend from the front face 8 to the side wall 9. The cutting member 3 is preferably cylindrical in shape, and the apertures 7 are preferably circular in cross-section. The apertures must be of such a size that a surgical thread can slide therethrough, and it has been found convenient to use apertures having a diameter of 0.6 mm. Where the apertures emerge through the side wall 9 the circular cross-section of the apertures will give rise to an opening which is elliptical in shape. The curved distal portion of each elliptical opening provides an arcuately curved cutting edge for cutting the thread, as will be explained further below.

The drawings show an example of the use of the cutting device of the present invention, in which the surgeon has inserted a surgical thread 10 through a U-shaped piece of a patient's tissue 11 and has tied a knot 12 therein. The procedure used to do this has left the two thread tails 13 extending through a passageway in the patient's body and out through a bodily opening. For example, if the thread has been inserted in the lining of the patient's stomach, the thread ends will extend through the patient's gullet and out through the mouth.

The thread cutter is then inserted into the endoscope, so that the cutting member 3 is located outwardly of the distal end thereof, and the mounting member 5 is located outwardly of the proximal end. The thread ends 13 are then passed through respective ones of the apertures 7, and the endoscope, with the thread cutter therein, is then inserted through the patient's mouth, insertion being continued until the cutting member 3 is adjacent the knot 12, a fact which can be ascertained by observation through the viewing channel of the endoscope. During this insertion process the thread tails 13 slide through the apertures 7, with the free ends thereof always continuing to extend out of the patient's mouth. In this way, the position is reached which is shown in FIG. 1.

The surgeon then pulls on the thread tails 13 to create a tension therein, whilst moving the thread cutting member away from the knot, and the endoscope towards the knot, as indicated by the respective arrows in FIG. 2. This has the effect of forcing the thread tails 13 against the curved cutting edges which, as mentioned above, are formed at the proximal ends of the passages 7. The fact that these cutting edges are curved means that the thread tails 13 tend to remain approximately central with respect to the length of the cutting edges. If the cutting edges were straight, with the opening in which they were formed being, say, rectangular, there would be a tendency for the thread tails 13 to slip to one or other end of the cutting edge, and this might impede an effective cutting action.

As shown in FIG. 3, the procedure just described has the effect of causing the thread tails 13 to be cut, and they can then be removed through the patient's mouth. The final result is shown diagrammatically in FIG. 4.

We claim:

1. A device for endoscopically cutting a surgical thread, which comprises a cutting member having proximal and distal ends and having at least one aperture extending therethrough of a size sufficient to permit the surgical thread to slide therethrough, the aperture having a proximally facing thread-cutting edge and the cutting member being movably mounted with respect to the distal end of an endoscope whereby the surgical thread is cut by proximal movement of the cutting member relative to the thread.

2. A device according to claim 1, wherein the thread-cutting edge is arcuate.

3. A device according to claim 2, wherein the said aperture meets a curved outer surface of the cutting member to define the said thread-cutting edge.

4. A device according to claim 3, wherein the cutting member is cylindrical and has at least one said aperture extending therethrough from a forward end face thereof to the cylindrical surface thereof.

5. A device according to claim 4, wherein a pair of said apertures is provided.

6. A device according to claim 5, wherein the apertures are diametrically opposite one another.

7. A device according to claim 1, wherein the said enabling means comprises an elongate member connected at one end to the cutting member and at the other end to a mounting member for operation by the user.

8. A device according to claim 7, wherein the said elongate member is surrounded by a sheath in which the said elongate member is slidable, the sheath being connected neither to the cutting member nor to the mounting member.

9. A device as recited in claim 1 wherein the distal end of the endoscope has a distal face and the thread is cut between the distal face and the proximally facing thread-cutting edges as the cutting member is moved proximally with respect to the distal end of the endoscope.

10. A method of cutting a surgical thread at a suture site within a patient comprising:

providing an endoscope having proximal and distal ends;

providing a cutting member having proximal arid distal ends and having at least one aperture extending therethrough of a size sufficient to permit the surgical thread to slide therethrough, the aperture having a proximally facing thread-cutting edge, and the cutting member being movably mounted with respect to the distal end of an endoscope, inserting the cutting member into and through the endoscope such that the cutting member protrudes at least slightly from the distal end of the endoscope;

inserting the surgical thread through the aperture(s) of the cutting member then holding the surgical thread in tension while advancing the cutting member and endoscope into the patient to the suture site;

withdrawing the cutting member proximally relative to the thread to cut the thread with the thread-cutting edge.

11. A method of cutting a surgical thread at a suture site within a patient comprising:

providing an endoscope having proximal and distal ends;

providing a cutting member having at least one thread-cutting edge and being movably mounted with respect to the distal end of the endoscope;

placing the surgical thread in tension;

moving the thread cutting member proximally relative to the distal end of the endoscope to cause the angle between the longitudinal axis of the thread and axis of movement of the cutting member to increase such that the thread becomes cut against the thread cutting edge.

12. A device for endoscopically cutting a surgical thread, which comprises a cutting member having at least one aperture extending therethrough of a size sufficient to permit the surgical thread to slide therethrough, the aperture having a single thread-cutting edge that is the sole means for cutting the thread and the cutting member being movably mounted with respect to the distal end of a flexible endoscope.

13. A device for cutting a surgical thread within a patient, which comprises a cutting member having proximal and distal ends and having at least one aperture extending therethrough of a size sufficient to permit the surgical thread to slide therethrough, the aperture having a proximally facing thread-cutting edge, and the cutting member being slidably receivable in a tubular shaft that is positionable to introduce the cutting member into the patient whereby the surgical thread is cut by proximal movement of the cutting member relative to the thread.

* * * * *